United States Patent [19]

Takematsu et al.

[11] Patent Number: 4,844,731
[45] Date of Patent: Jul. 4, 1989

[54] TRIAZINE DERIVATIVES

[75] Inventors: Tetsuo Takematsu, Utsunomiya; Masahiro Nishii; Izumi Kobayashi, both of Chiba, all of Japan

[73] Assignee: Idemitsu Company Co., Ltd., Tokyo, Japan

[21] Appl. No.: 132,212

[22] Filed: Dec. 14, 1987

[30] Foreign Application Priority Data

Dec. 27, 1986 [JP]  Japan ................................ 61-311265

[51] Int. Cl.$^4$ .................. A01N 43/70; C07D 251/50; C07D 251/52
[52] U.S. Cl. ......................................... 71/93; 544/208
[58] Field of Search ............................. 71/93; 544/208

[56] References Cited

U.S. PATENT DOCUMENTS 3,310,557 3/1967 Kleeman .............................. 544/208
3,746,710 7/1973 Kuhne et al. ........................ 544/208

Primary Examiner—John M. Ford
Attorney, Agent, or Firm—Frishauf, Holtz, Goodman & Woodward

[57] ABSTRACT

Novel triazine derivatives represented by the general formula (I):

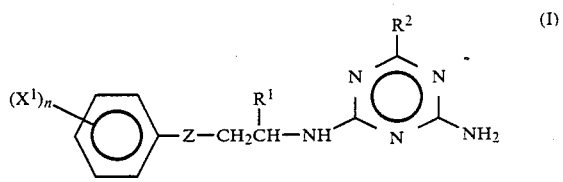

(wherein all the symbols are as defined in the appended claims), and herbicides containing the triazine derivatives of the general formula (I) as effective component. These triazine derivatives can exhibit their herbicidal activity against various types of weeds from annual weeds to perennial weeds while causing no injury against paddy rice plants. Thus the herbicides of the present invention have advantages in that the herbicidal effect is great, the chemical damage is low, and the weed-killing spectral width is broad.

39 Claims, No Drawings

TRIAZINE DERIVATIVES

BACKGROUND OF THE INVENTION

The present invention relates to triazine derivatives which are novel compounds, and herbicides containing said derivatives as effective component.

Various triazine-based herbicides have heretofore been known. For example, 2-methylthio-4,6-bis(alkylamino)-s-triazine derivatives are known to be effective herbicides having a high weed control activity. However, the effect of 2-methylthio-4,6-bis(ethylamino)-s-triazine, for example, greatly varies with conditions such as the type of soil and temperature. In more detail, when used in a mild district, it causes phytotoxicity (injury) even in the commonly used amount, and in a cold district, its effect is exhibited only insufficiently. Thus 2-methylthio-4,6-bis(ethylamino)-s-triazine has a disadvantage in that it can be applied as a herbicide only in a limited district.

SUMMARY OF THE INVENTION

The present invention is intended to overcome the prior art problems and an object of the present invention is to provide novel herbicides which can exhibit its herbicidal activity nearly equal under various types of soil and temperature conditions, and also can exhibit its herbicidal activity against various types of weeds from annual weeds to perennial weeds while causing no injury against paddy rice plants.

It has been found that the object is attained by using specified triazine derivatives having a phenoxy group or a phenylthio group.

The present invention relates to triazine derivatives represented by the general formula (I):

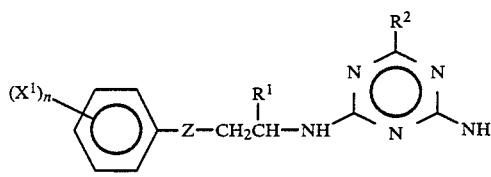

(wherein $X^1$ is a hydrogen atom, an alkyl group having 1 to 4 carbon atoms, an alkoxy group having 1 to 4 carbon atoms, a halogen atom, a haloalkyl group having 1 to 4 carbon atoms, a phenyl group, or a phenoxy group; n is an integer of 1 to 5, and when n is plural, $X^1$s may be the same or different; Z is an oxygen atom or a sulfur atom; $R^1$ is an alkyl group having 1 to 4 carbon atoms; and $R^2$ is a halogen atom, an alkoxy group having 1 to 4 carbon atoms, or an alkylthio group having 1 to 4 carbon atoms).

The present invention further relates to herbicides containing the above triazine derivatives as herbicidally effective component.

DETAILED DESCRIPTION OF THE INVENTION

In the general formula (I), $X^1$ is a hydrogen atom, an alkyl group having 1 to 4 carbon atoms (e.g., a methyl group, an ethyl group, a n-propyl group, an isopropyl group, a n-butyl group, an isobutyl group, a sec-butyl group and a tert-butyl group), an alkoxy group having 1 to 4 carbon atoms (e.g., a methoxy group, an ethoxy group, a propoxy group and a butoxy group), a halogen atom (e.g., a chlorine atom, a bromine atom, a fluorine atom and an iodine atom), a haloalkyl group having 1 to 4 carbon atoms (e.g., a trifluoromethyl group, a trichloromethyl group, a monochloromethyl group, a monobromomethyl group, a monofluoromethyl group and a pentafluoroethyl group), a phenyl group, or a phenoxy group.

Of these groups, an alkyl group having 1 to 4 carbon atoms, an alkoxy group having 1 to 4 carbon atoms, and a haloalkyl group having 1 to 4 carbon atoms are preferred.

n indicates the number of substitutents for $X^1$ and is an integer of 1 to 5, preferably 1 or 2. When n is 2 or more, $X^1$s may be the same or different. $X^1$ may be located at any position of ortho, meta and para relative to Z; it is relatively preferred to be located at the meta-position.

Z is an oxygen atom or a sulfur atom.

$R^1$ is an alkyl group having 1 to 4 carbon atoms (e.g., a methyl group, an ethyl group, a n-propyl group, an isopropyl group, a n-butyl group, an isobutyl group, a sec-butyl group, and a tert-butyl group). Of these groups, a methyl group and an ethyl group are preferred.

$R^2$ is a halogen atom (e.g., a chlorine atom, a bromine atom, a fluorine atom and an iodine atom), an alkoxy group having 1 to 4 carbon atoms (e.g., a methoxy group, an ethoxy group, a propoxy group and a butoxy group), or an alkylthio group having 1 to 4 carbon atoms (e.g., a methylthio group, an ethylthio group, a propylthio group and a butylthio group). Of these groups, an alkylthio group having 1 to 4 carbon atoms preferred, with a methylthio group and an ethylthio group being particularly preferred.

In addition to compounds obtained in Preparation Examples as undermentioned, representative examples of the triazine derivatives represented by the general formula (I) are as follows: 2-amino-4-chloro-6-[2-(3'-ethylphenoxy)isopropylamino]-s-triazine; 2-amino-4-chloro-6-[2-(3'-sec-butylphenoxy)isopropylamino]-s-triazine; 2-amino-4-chloro-6-[2-(3'-isopropylphenoxy)isopropylamino]-s-triazine; 2-amino-4-chloro-6-[2-(3'-isopropoxyphenoxy)isopropylamino]-s-triazine; 2-amino-4-chloro-6-[2-(3'-t-butoxyphenoxy)isopropylamino]-s-triazine; 2-amino-4-chloro-6-[2-(3'-ethoxyphenoxy)isopropylamino]-s-triazine; 2-amino-4-chloro-6-[2-(3'-bromophenoxy)isopropylamino]-s-triazine; 2-amino-4-chloro-6-[2-(3'-fluorophenoxy)isopropylamino]-s-triazine; 2-amino-4-chloro-6-[2-(3'-monochloromethylphenoxy)isopropylamino]-s-triazine; 2-amino-4-chloro-6-[2-(3'-pentafluoroethylphenoxy)isopropylamino]-s-triazine; 2-amino-4-chloro-6-[2-(3',5'-dimethoxyphenoxy)isopropylamino]-s-triazine; 2-amino-4-chloro-6-[2-(3'-methyl-5'-methoxyphenoxy)isopropylamino]-s-triazine; 2-amino-4-chloro-6-[2(3',5'-dimethylphenoxy)-1-ethyl-ethylamino]-s-triazine; 2-amino-4-chloro-6-[2-(2',5'-dimethylphenoxy)-1-ethyl-ethylamino]-s-triazine; 2-amino-4-chloro-6-[2-(3',5'-dimethylphenylthio)isopropylamino]-s-triazine; 2-amino-4-chloro-6-[2-(2',5'-dimethylphenylthio)isopropylamino]-s-triazine; 2-amino-4-chloro-6-[2-(3'-trifluoromethylphenylthio)isopropylamino]-s-triazine; 2-amino-4-methylthio-6-[2-(3'-ethylphenoxy)isopropylamino]-s-triazine; 2-amino-4-methylthio-6-[2-(3'-sec-butylphenoxy)isopropylamino]-s-triazine; 2-amino-4-methylthio-6-[2-(3'-isopropylphenoxy)isopropylamino]-s-triazine; 2-amino-4-methylthio-6-[2-(3'-isopropoxyphenoxy)isopropylamino]-s-triazine; 2- amino-4-methylthio-6-[2-(3'-t-butoxyphenoxy)isopropylamino]-s-triazine; 2-amino-4-methylthio-6-[2-(3'-ethoxyphenoxy)isopropylamino]-s-triazine; 2-amino-4-methylthio-6-[2-(3'-bromophenoxy)isopropylamino]-s-triazine; 2-amino-4-methylthio-6-[2-(3'-fluorophenoxy)isopropylamino]-s-triazine; 2-amino-4-methylthio-6-[2-(3'-monochloromethylphenoxy)isopropylamino]-s-triazine; 2-amino-4-methylthio-6-[2-(3'-pentafluoroethylphenoxy)isopropylamino]-s-triazine; 2-amino-4-methylthio-6-[2-(3',5'-dimethoxyphenoxy)isopropylamino]-s-triazine; 2-amino-4-methylthio-6-[2-(3'-methyl-5'-methoxyphenoxy)isopropylamino]-s-triazine; 2-amino-4-methylthio-6-[2-(3',5'-dimethylphenoxy)-1-ethyl-ethylamino]-s-triazine; 2-amino-4-methylthio-6-[2-(2',5'-dimethylphenoxy)-1-ethyl-ethylamino]-s-triazine; 2-amino-4-methylthio-6-[2-(3',5'-dimethylphenylthio)isopropylamino]-s-triazine; 2-amino-4-methlthio-6-[2-(2',5'-dimethylphenylthio)isopropylamino]-s-triazine; 2-amino-4-methylthio-6-[2-(3'-trifluoromethylphenylthio)isopropylamino]-s-triazine; 2-amino-4-ethylthio-6-[2-(3',5'-dimethylphenoxy)isopropylamino]-s-triazine; 2-amino-4-ethoxy-6-[2-(3',5'-dimethlphenoxy)isopropylamino]-s-triazine; 2-amino-4-ethylthio-6-[2-(2',5'-dimethylphenoxy)isopropylamino]-s-triazine; 2-amino-4-ethoxy-6-[2-(2',5'-dimethylphenoxy)isopropylamino]-s-triazine; 2-amino-4-ethylthio-6-[2-(3'-trifluoromethylphenoxy)isopropylamino]-s-triazine; 2-amino-4-ethoxy-6-[2-(3'-trifluoromethylphenoxy)isopropylamino]-s-triazine. .

The triazine derivatives of the general formula (I) can be divided into three groups: (1) halogen-containing triazine derivatives represented by the general formula (I-A):

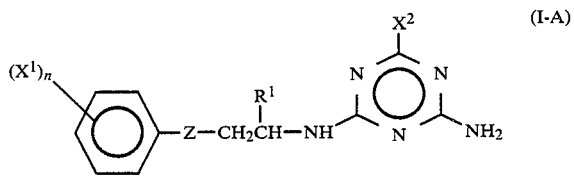

(wherein $X^1$, Z, $R^1$ and n are as defined above, and $X^2$ is a halogen atom); (2) sulfur-containing triazine derivatives represented by the general formula (I-B):

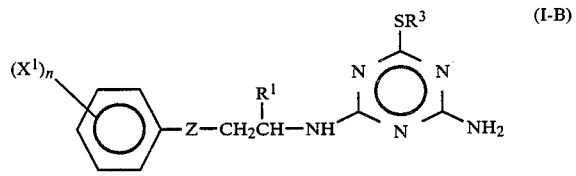

(wherein $X^1$, Z, $R^1$ and n are as defined above, and $R^3$ is an alkyl group having 1 to 4 carbon atoms); and (3) oxygen-containing triazine derivatives represented by the general formula (I-C):

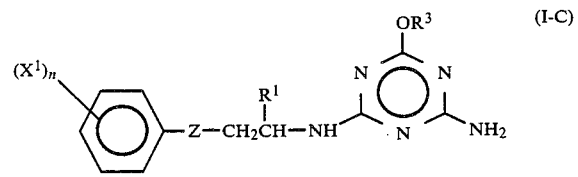

(wherein $X^1$, Z, $R^1$, $R^3$ and are as defined above).

Typical methods for efficiently preparing the triazine derivatives of the present invention; i.e., the triazine derivatives of the general formulae (I-A), (I-B) and (I-C) are described below.

The triazine derivatives of the general formula (I-A) can be prepared by reacting alkylamine derivatives of the general formula (II):

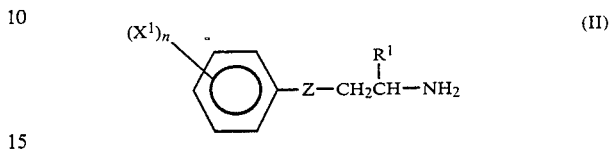

(wherein $X^1$Z, $R^1$ and n are as defined above) and dihalogenated aminotriazines of the general formula (III):

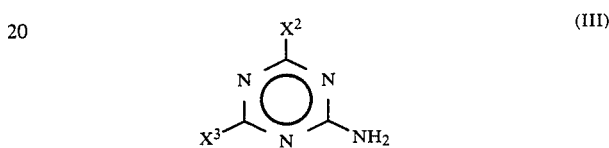

(wherein $X^2$ is as defined above, and $X^3$ is a halogen atom). This method is hereinafter referred to as "Method (1)".

In the method (1), the alkylamine derivatives of the general formula (II) and the dihalogenated aminotriazines of the general formula (III) are used in nearly equimolar ratios. A solvent is not necessarily needed; if desired, ketones such as acetone, methyl ethyl ketone and cyclohexanone; aliphatic hydrocarbons such as n-hexane and n-heptane; cyclic hydrocarbons such as benzene, decalin and alkylnaphthalene; chlorinated hydrocarbons such as carbon tetrachloride and ethylene dichloride; ethers such as tetrahydrofuran and dioxane; and the like can be used. It is effective to add a deacidizing agent (a dehydrochlorinating agent), such as sodium carbonate, sodium hydrogencarbonate and triethylamine. The reaction temperature is not critical; the reaction is usually carried out within the temperature range of 10° to 100° C. although it can be carried out at lower temperatures or high temperatures.

In accordance with the method (1), the halogen-containing triazine derivatives represented by the general formula (I-A) can be prepared in high purity and high yield.

In addition to compounds obtained in Reference Examples as undermentioned, representative examples of the alkylamine derivatives of the general formula (II) which are used in the method (1) are as follows: 2-(3-ethylphenoxy)isopropylamine; 2-(3-sec-butylphenoxy)isopropylamine; 2-(3-isopropylphenoxy)-isopropylamine; 2-(3-isopropoxyphenoxy)isopropylamine; 2-(3-t-butoxyphenoxy)isopropylamine; 2-(3-ethoxyphenoxy)isopropylamine; 2-(3-bromophenoxy)isopropylamine; 2-(3-fluorophenoxy)isopropylamine; 2-(3-monochloromethylphenoxy)isopropylamine; 2-(3-pentafluoroethylphenoxy)isopropylamine; 2-(3,5-dimethoxyphenoxy)isopropylamine; 2-(3-methoxy-5-methylphenoxy)isopropylamine; 2-(3,5-dimethylphenoxy)-1-ethyl-ethylamine; 2-(2,5-dimethylphenoxy)-1-ethyl-ethylamine; 2-(3,5-dimethylphenylthio)isopropylamine; 2-(2,5-dimethyl-phenylthio)isopropylamine; 2-(3-trifluoromethylphenylthio)isopropylamine.

The alkylamine derivatives of the general formula (II), i.e., 2-phenoxyalkylamine and its derivatives, and 2-phenylthioalkylamine and its derivatives can be prepared by various methods. For example, they can be prepared by reacting phenoxyketones or phenylthioketones represented by the general formula (VIII):

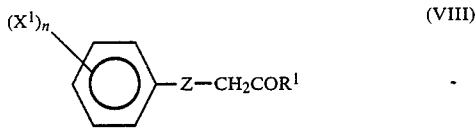

(wherein $X^1$, $Z$, $R^1$ and n are as defined above) with ammonium formate or formamide and formic acid to form N-formylalkylamine derivatives represented by the general formula (IX):

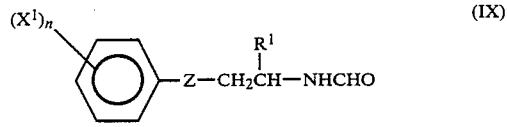

(wherein $X^1$, $Z$, $R^1$ and n are as defined above), and then hydrolyzing the N-formylalkylamine derivatives by heating in the presence of an acid such as concentrated hydrochloric acid or caustic alkali such as oaustic soda.

The alkylamine derivatives of the general formula (II) can also be prepared by reacting phenoxyketones or phenylthioketones represented by the general formula (VIII) with ammonium acetate and sodium borocyanate.

The dihalogenated aminotriazines of the general formula (III), i.e., 2-amino-4,6-dihalogeno-s-triazine, include 2-amino-4,6-dichloro-s-triazine. This dihalogenated aminotriazine can be obtained by reacting cyanuric halide such as cyanuric chloride with ammonia.

The sulfur-containing triazine derivatives of the general formula (I-B) can be prepared by reacting the halogen-containing triazine derivatives of the general formula (I-A) with alkylmercaptan represented by the general formula (IV):

$$R^3SH \qquad (IV)$$

(wherein $R^3$ is as defined above), or alkylmercaptide represented by the general formula (V):

$$(R^3S)_mM \qquad (V)$$

(wherein $R^3$ is as defined above, M is an alkali metal or an alkali earth metal, and m is the valance of M). This method is hereinafter referred to as "Method (2)".

As the halogen-containing triazine derivatives of the general formula (I-A), as well as those prepared by the method (1), those prepared by other suitable methods can be used.

Examples of the alkylmercaptan are methylmercaptan, ethylmercaptan, and propylmercaptan. Examples of the alkylmercaptide are sodium methylmercaptide ($CH_3SNa$), potassium methylmercaptide ($CH_3SK$), magnesium methylmercaptide (($CH_3S)_2Mg$), sodium ethylmercaptide ($C_2H_5SNa$), potassium ethylmercaptide ($C_2H_5SK$), and magnesium ethylmercaptide (($C_2H_5S)_2Mg$).

In the method (2), when alkylmercaptan is used, it is preferred that the reaction be carried out in the presence of caustic alkali such as sodium hydroxide and potassium hydroxide.

The mixing ratio of the halogen-containing triazine derivatives of the general formula (I-A) to the alkylmercaptan or alkylmercaptide is not critical; usually they are used in a nearly equal molar ratio. The reaction can be carried out in the absence or presence of a solvent. Examples of solvents which can be used include isopropylacohol, dimethlformamide, toluene, xylene and benzene. The reaction temperature is not critical; the reaction can be carried out within the temperature range of 10° to 150° C. although it can be carried out at lower temperatures or higher temperatures.

After the completion of the reaction, water is added to the reaction mixture and extracted with solvent such as ethyl acetate. Upon purification of the product obtained by silica gel column chromatography, the sulfur-containing triazine derivatives of the general formula (I-B) can be obtained in high purity and high yield.

The oxygen-containing triazine derivatives of the general formula (I-C) can be prepared by reacting the halogen-containing triazine derivatives of the general formula (I-A) with alcohols represented by the general formula (VI):

$$R^3OH \qquad (VI)$$

(wherein $R^3$ is as defined above), or metal alkoxides represented by the general formula (VII):

$$(R^3O)_mM \qquad (VII)$$

(wherein $R^3$, M and m are as defined above). This method is hereinafter referred to as "Method (3)".

As the halogen-containing triazine derivatives of the general formula (I-A), as well as those prepared by the method (41), those prepared by other suitable methods can be used.

Representative examples of the alcohols represented by the general formula (VI) are methyl alcohol, ethyl alcohol and propyl alcohol. Representative examples of the alkoxides represented by the general formula (VII) are sodium methoxide ($CH_3ONa$), potassium methoxide ($CH_3OK$), calcium methoxide (($CH_3O)_2Ca$), sodium ethoxide ($C_2H_5ONa$), potassium ethoxide ($C_2H_5OK$), and potassium ethoxide (($C_2H_5O)_2Ca$).

In the method (3), when alcohol is used, it is preferred for the reaction to be carried out in the presence of alkali metals such as metallic sodium and metallic potassium.

The mixing ratio of the halogen-containing triazine derivatives of the general formula (I-A) to the alcohols of the general formula (VI) or alkoxides of the general formula (VII) is not critical; usually they are used in a nearly equimolar ratio. The reaction can be carried out in the absence or presence of a solvent. Preferred examples of the solvents which can be used are methyl alcohol, ethyl alcohol, and isopropyl alcohol. The reaction temperature is not critical; usually the reaction is carried out within the temperature range of 10° to 100° C. although it can be carried out at lower temperatures or higher temperatures.

After the completion of the reaction, solvent is distilled away and the residue is extracted with solvent such as chloroform. Upon purification of the product obtained by silica gel column chromatography, followed by drying, the oxygen-containing triazine derivatives of the general formula (I-C) can be obtained in high purity and high yield.

The triazine derivatives of the general formula (I) inhibit germination and growth of weeds and further have high selectivity, and thus are suitable as herbicides. Moreover, the triazine derivatives of the general formula (I) exhibit excellent herbicidal activity against annual broadloaf weeds such as Rotala indica(Willd.-)Koehne var. uligirosa(Miq.)Koehne., Lindernia pyxidaria L. and Monochoria vaginalis Presl var. plantaginea(Robx.)Solms-Laub., species of Cyperaceae such as Cyperus difformis L., and Gramineae such as Echinochloa crus-galli L., as well as perennial weeds such as Scirpus juncoides Roxb. var. Hotarui Ohwi, Cyperus serotinus Rottb. and Sagittaria pygmaea Miq. which are now considered to be difficult to control, without causing phytotoxicity to paddy rice plants.

Herbicides of the present invention comprises (i) a herbicidal carrier, and (ii) a herbicidally effective amount of the triazine derivative of the general formula (I).

The herbicides of the present invention can be applied in the form of compositions such as a wettable powder, an emulsifiable concentrate, dust, granule and the like. Such compositions are prepared by mixing the triazine derivative of the general formula (I) as the effective component with a liquid carrier such as an organic solvent and the like or a solid carrier such as a mineral powder and the like. Addition of a surfactant is preferred to impart the properties of ready emulsifying, dispersing, spreading and the like to the preparations.

When the herbicides of this invention are applied in the form of wettable powder, the herbicides usually comprise 10–55 parts by weight of the triazine derivative as the effective component, 40–88 parts by weight of a solid carrier and 2–5 parts by weight of a surfactant. When the herbicides are applied in the form of emulsifiable concentrate, the herbicides usually comprise 20–50 parts by weight of the triazine derivative as the effective component, 35–75 parts by weight of a solvent and 5–15 parts by weight of a surfactant.

When the herbicides are applied in the form of dust, the herbicides usually comprise 1–15 parts by weight of the triazine derivative as the effective component, 80–97 parts by weight of a solid carrier and 2–5 parts by weight of a surfactant. When the herbicides are applied in the form of granule, the herbicides usually comprise 0.1–15 parts by weight of the triazine derivative as the effective component, 80–97.9 parts by weight of a solid carrier and 2–5 parts by weight of a surfactant.

A mineral powder can be used as the solid carrier described above. The mineral powder includes oxide such as diatomaceous earth and slaked lime, phosphate such as apatite, sulfate such as gypsum, and silicate such as talc, pyrophyllite, clay, kaolin, bentonite, acid clay, white carbon, quartz powder and silica powder.

An organic solvent can be used as the solvent described above. The organic solvent includes an aromatic hydrocarbon such as xylene, toluene and benzene, a chlorinated hydrocarbon such as o-chlorotoluene, trichloromethane and trichloroethylene, an alcohol such as cyclohexanol, amylalcohol and ethylene glycol, a ketone such as isophorone, cyclohexanone and cyclohexenylcyclohexanone, an ether such as butylcellosolve, dimethylether and methylethylether, an ester such as isopropyl acetate, benzyl acetate and methyl phthalate, an amide such as dimethylformamide, and a mixture thereof. The above surfactant includes various kinds of surfactant, that is anion type, cation type, nonion type and amphoteric ion type (e.g. amino acid and betaine).

The novel triazine derivatives of the general formula (I) of the present invention, which are a novel compound, is high weed control activity against annual weeds as well as perennial weeds and exhibits high selectivity and thus is useful as a herbicide not causing any injury against paddy rice plants.

In the herbicide of the present invention, as the effective component, other herbicidal materials can be used in combination with the triazine derivative of the general formula (I). These other herbicidal materials include conventionally used herbicides. Examples of such conventionally used herbicides are a pheoxy-based herbicide, a diphenyl ether-based herbicide, a triazine-based herbicide, a urea-based herbicide, a carbamate-based herbicide, a thiol carbamate-based herbicide, an acid anilide-based herbicide, a pyrazole-based herbicide, phosphoric acid-based herbicide, a sulfonylurea-based herbicide, and an oxadiazone-based herbicide.

The herbicides of the present invention can be used in admixture with insecticides, germicides, plant growth regulating agents, fertilizers and so forth, if necessary.

The present invention is described in greater detail with reference to the following examples.

REFERENCE EXAMPLE 1

Preparation of Alkylamine Derivatives 6.56 g (40 mmol) of (3-methylphenoxy)acetone, 21.6 g (242 mmol) of ammonium acetate and 1.76 g (28 mmol) of sodium borocyanate were dissolved in 60 ml of anhydrous methanol and stirred for 2 hours at room temperature. Then, 40 ml of concentrated hydrochloric acid was added to the above reaction mixture, and the methanol was then distilled away under reduced pressure. The residue thus obtained was placed in 100 ml of water and washed with 100 ml of ethyl ether. The aqueous layer thus obtained was made alkaline by adding potassium hydroxide and extracted three times with 40 ml of ethyl ether.

The ethyl ether layer was washed with water and dried over anhydrous sodium sulfate, and the ethyl ether was distilled away under reduced pressure to obtain 2.31 g of 2-(3-methylphenoxy)isopropylamine having the formula:

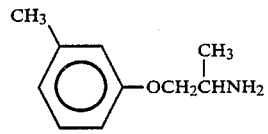

(yield 35%).

REFERENCE EXAMPLES 2 TO 15

The procedure of Reference Example 1 was repeated with the exception the keones shown in Table 1 (phenoxyacetones and phenylthioacetones) were used in place of the (3-methylphenoxy)acetone.

The results are shown in Table 1.

TABLE 1

| No. | Ketones as Starting Material | Alkylamine Derivatives produced | | | |
|---|---|---|---|---|---|
| | | Name | Amount (g) | Yield (%) | Structural |
| Reference Example 2 | 2-CH₃-C₆H₄-OCH₂COCH₃ | 2-(2-Methylphenoxy)isopropylamine | 2.58 | 39 | 2-CH₃-C₆H₄-OCH₂CH(CH₃)NH₂ |
| Reference Example 3 | 4-H₃C-C₆H₄-OCH₂COCH₃ | 2-(4-Methylphenoxy)isopropylamine | 2.45 | 37 | 4-H₃C-C₆H₄-OCH₂CH(CH₃)NH₂ |
| Reference Example 4 | 2,3-(H₃C)₂-C₆H₃-OCH₂COCH₃ | 2-(2,3-Dimethylphenoxy)isoproplyamine | 3.37 | 51 | 2,3-(H₃C)₂-C₆H₃-OCH₂CH(CH₃)NH₂ |
| Reference Example 5 | C₆H₅-OCH₂COCH₃ | 2-Phenoxyisopropylamine | 4.48 | 74 | C₆H₅-OCH₂CH(CH₃)NH₂ |
| Reference Example 6 | 3,4-(H₃C)₂-C₆H₃-OCH₂COCH₃ | 2-(3,4-Dimethylphenoxy)isopropylamine | 2.87 | 40 | 3,4-(H₃C)₂-C₆H₃-OCH₂CH(CH₃)NH₂ |
| Reference Example 7 | 3-CH₃O-C₆H₄-OCH₂COCH₃ | 2-(3-Methoxyphenoxy)isopropylamine | 2.41 | 36 | 3-CH₃O-C₆H₄-OCH₂CH(CH₃)NH₂ |
| Reference Example 8 | 3-Cl-C₆H₄-OCH₂COCH₃ | 2-(3-Chlorophenoxy)isopropylamine | 4.75 | 64 | 3-Cl-C₆H₄-OCH₂CH(CH₃)NH₂ |
| Reference Example 9 | 2,5-(H₃C)₂-C₆H₃-OCH₂COCH₃ | 2-(2,5-Dimethylphenoxy)isopropylamine | 3.15 | 44 | 2,5-(H₃C)₂-C₆H₃-OCH₂CH(CH₃)NH₂ |
| Reference Example 10 | 3,5-(H₃C)₂-C₆H₃-OCH₂COCH₃ | 2-(3,5-Dimethylphenoxy)isopropylamine | 2.34 | 33 | 3,5-(H₃C)₂-C₆H₃-OCH₂CH(CH₃)NH₂ |
| Reference Example 11 | 3-(CH₃)₃C-C₆H₄-OCH₂COCH₃ | 2-(2,3-t-Butylphenoxy)isopropylamine | 3.32 | 40 | 3-(CH₃)₃C-C₆H₄-OCH₂CH(CH₃)NH₂ |

TABLE 1-continued

| No. | Ketones as Starting Material | Alkylamine Derivatives produced | | | |
|---|---|---|---|---|---|
| | | Name | Amount (g) | Yield (%) | Structural |
| Reference Example 12 | [phenyl]-[phenyl]-OCH₃COCH₃ | 2-(3-Phenylphenoxy)isopropylamine | 3.84 | 42 | [phenyl]-[phenyl]-OCH₂CH(CH₃)NH₂ |
| Reference Example 13 | [phenyl]-O-[phenyl]-OCH₃COCH₃ | 2-(3-phenoxyphenoxy)isopropylamine | 3.91 | 40 | [phenyl]-O-[phenyl]-OCH₂CH(CH₃)NH₂ |
| Reference Example 14 | F₃C-[phenyl]-OCH₃COCH₃ | 2-(3-Trifluoromethyl-phenoxy)isopropylamine | 3.60 | 41 | F₃C-[phenyl]-OCH₂CH(CH₃)NH₂ |
| Reference Example 15 | CH₃-[phenyl]-SCH₂COCH₃ | 2-(2-Methylphenylthio)isopropylamine | 3.12 | 43 | CH₃-[phenyl]-SCH₂CH(CH₃)NH₂ |

PREPARATION EXAMPLE 1

In 5.5 g of acetone was dissolved 1.64 g (10 mmol) of 2-amino-4,6-dichloro-s-triazine, and 1.65 g (10 mmol) of 2-(3'-methylphenoxy)isopropylamine as obtained in Reference Example 1 was added thereto. Subsequently a suspension of 0.84 g (10 mmol) of sodium hydrogencarbonate in 6.0 g of water was added to the above solution while stirring at 0°–5° C. Then the resulting mixture was gradually heated to 50° C. over 1 hour.

After heating, the mixture was cooled to yield a product. This product was separated, washed with water and then recrystallized from an ethanol/water mixture to obtain 2.73 g of white crystals of 2-amino-4-chloro-6-[2-(3'-methylphenoxy)isopropylamino]-s-triazine (Compound 1) (yield, 93%).

The structural formula and the analytical results of the above compound are shown in Table 2.

PREPARATION EXAMPLES 2 TO 15

The procedure of Preparation Example 1 was repeated wherein the alkylamines prepared in Reference Examples 2 to 15 were each used in place of 2-(3'-methylphenoxy)isopropylamine, thereby preparing the corresponding 2-amino-4-chloro-6-alkylamino-s-triazines (Compounds 2 to 15). The structural formula and the analytical results of each of the compounds as obtained above are shown in Table 2.

PREPARATION EXAMPLE 16

To a mixture of 9.0 g of isopropanol and 6.0 g of sodium methylmercaptide having a concentration of 15% which had been heated to 50°–60° C. was added 2.94 g (10 mmol) of 2-amino-4-chloro-6-[2-(3'-methylphenoxy)isopropylamino]-s-triazine as prepared in Preparation Example 1 while stirring. The resulting reaction mixture was heated under reflux for 3 hours while stirring. After the reaction mixture was cooled to 10° C., 100 ml of water was added thereto. The resulting mixture was extracted three times with 20 ml of ethyl acetate. The ethyl acetate layer was drived over anhydrous sodium sulfate and then the solvent was distilled away under reduced pressure. The residue was purified by developing it by silica gal column chromatography (developing solvent, toluene/ethyl acetate=8/2) to obtain 2.81 g of 2-amino-4-methylthio-[2-(3'-methylphenoxy)isopropylamino]-s-triazine in a colorless resinoid form (Compound 16) (yield, 92%).

The structural formula and the analytical results of the compound are shown in Tables 2 and 3.

PREPARATION EXAMPLES 17 TO 30

The procedure of Preparation Example 16 was repeated wherein the compounds prepared in Preparation Examples 2 to 15 were each used in place of 2-amino-4-chloro-6-[2-(3'-methylphenoxy)isopropylamino]-s-triazine, thereby the corresponding 2-amino-4-methylthio-6-alkylamino-s-triazines (Compounds 17 to 30). The structural formula and the analytical results of each of the compounds as obtained above are shown in Tables 2 and 3.

PREPARATION EXAMPLE 31

In 20 ml of methanol was dissolved 2.94 g (10 mmol) of 2-amino-4-chloro-6-[2-(3'-methylphenoxy)isopropylamino]-s-triazine (Compound 1) as prepared in Preparation Example 1, and then 2.31 g (12 mmol) of 28% sodium methoxide was added thereto. The resulting mixture was heated under reflux with stirring for 14 hours. After the methanol was distilled away under reduced pressure, the residue was dissolved in 50 ml of chloroform and washed with water. The chloroform layer was dried over anhydrous sodium sulfate, and then the solvent was distilled away under reduced pressure. The residue was purified by developing it by silica gel column chromatography (developing solvent: toluene/ethyl acetate=8/2), and then was recrystallized from an ethanol/water mixture to obtain 2.72 g of white crystals of 2-amino-4-methoxy-6-[2-(3'-methylphenoxy)isopropylamino]-s-triazine (Compound 31) (yield, 94%).

The structural formula and the analytical results of the compound are shown in Table 2.

TABLE 2
Triazine Derivatives

| Preparation Example No. | Compound produced | Name | Amount (g) | Yield (%) | Melting Point (°C.) | Elemental Analysis*(%) | | | Structure | Molecular Formula | Molecular Weight |
|---|---|---|---|---|---|---|---|---|---|---|---|
| | | | | | | C | H | N | | | |
| 1 | Compound 1 | 2-Amino-4-chloro-6-[2-(3'-methylphenoxy)-1-methyl-ethylamino]-s-triazine | 2.73 | 93 | 159.1~161.9 | 53.5 (53.2) | 5.3 (5.5) | 24.0 (23.8) | 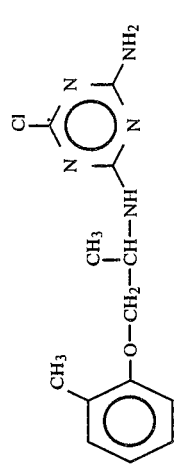 | $C_{13}H_{16}N_5OCl$ | 293.8 |
| 2 | Compound 2 | 2-Amino-4-chloro-6-[2-(2'-methylphenoxy)-1-methyl-ethylamino]-s-triazine | 2.70 | 92 | 176.3~177.8 | 53.6 (53.2) | 5.4 (5.5) | 23.6 (23.8) | 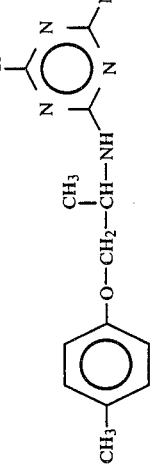 | $C_{13}H_{16}N_5OCl$ | 293.8 |
| 3 | Compound 3 | 2-Amino-4-chloro-6-[2-(4'-methylphenoxy)-1-methyl-ethylamino]-s-triazine | 2.76 | 94 | 131.5~133.0 | 53.0 (53.2) | 5.7 (5.5) | 23.6 (23.8) | 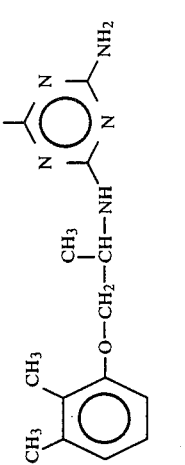 | $C_{13}H_{16}N_5OCl$ | 293.8 |
| 4 | Compound 4 | 2-Amino-4-chloro-6-[2-(2',3'-dimethyl-phenoxy)-1-methyl-ethylamino]-s-triazine | 2.86 | 93 | 145.0~146.5 | 54.3 (54.6) | 5.7 (5.9) | 23.0 (22.8) | 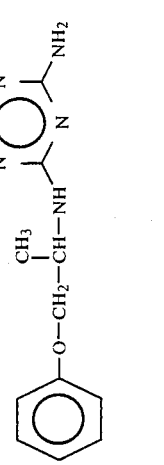 | $C_{14}H_{18}N_5OCl$ | 307.8 |
| 5 | Compound 5 | 2-Amino-4-chloro-6-(2-phenoxy-1-methyl-ethylamino)-s-triazine | 2.57 | 92 | 154.8~156.3 | 51.1 (51.5) | 5.2 (5.0) | 25.3 (25.0) | 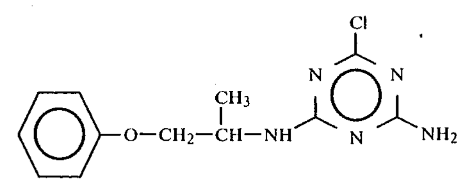 | $C_{12}H_{14}N_5OCl$ | 279.7 |

TABLE 2-continued

Triazine Derivatives

| Preparation Example No. | Compound produced | Name | Amount (g) | Yield (%) | Melting Point (°C.) | Elemental Analysis*(%) C | H | N | Structure | Molecular Formula | Molecular Weight |
|---|---|---|---|---|---|---|---|---|---|---|---|
| 6 | Compound 6 | 2-Amino-4-chloro-6-[2-(3',4'-dimethyl-phenoxy)-1-methyl-ethylamino]-s-triazine | 2.89 | 94 | 177.7~179.0 | 54.8 (54.6) | 5.7 (5.9) | 23.0 (22.8) | 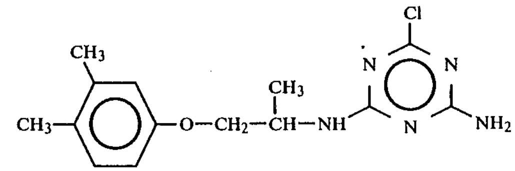 | $C_{14}H_{18}N_5OCl$ | 307.8 |
| 7 | Compound 7 | 2-Amino-4-chloro-6-[2-(3'-methoxy-phenoxy)-1-methyl-ethylamino]-s-triazine | 2.88 | 93 | 137.5~139.0 | 50.1 (50.4) | 5.1 (5.2) | 22.9 (22.6) | 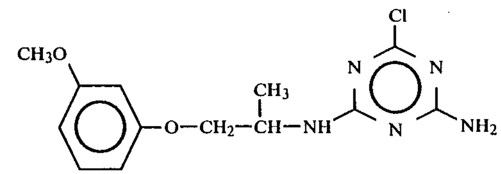 | $C_{13}H_{16}N_5O_2Cl$ | 309.8 |
| 8 | Compound 8 | 2-Amino-4-chloro-6-[2-(3'-chlorophenoxy)-1-methyl-ethylamino]-s-triazine | 2.89 | 92 | 155.5~160.3 | 45.6 (45.9) | 4.4 (4.2) | 22.0 (22.3) | 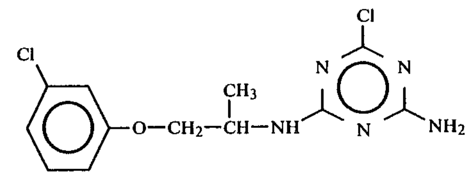 | $C_{12}H_{13}N_5OCl_2$ | 314.2 |
| 9 | Compound 9 | 2-Amino-4-chloro-6-[2-(2',5'-dimethyl-phenoxy)-1-methyl-ethylamino]-s-triazine | 2.83 | 92 | 114.9~116.9 | 54.7 (54.6) | 5.7 (5.9) | 22.5 (22.8) | 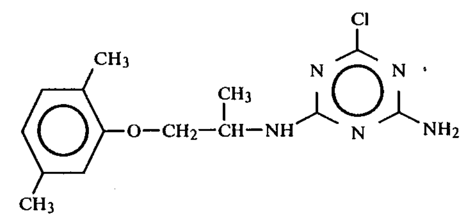 | $C_{14}H_{18}N_5OCl$ | 307.8 |
| 10 | Compound 10 | 2-Amino-4-chloro-6-[2-(3',5'-dimethyl-phenoxy)-1-methyl-ethylamino]-s-triazine | 2.86 | 93 | 149.2~151.2 | 54.3 (54.6) | 6.0 (5.9) | 22.9 (22.8) | 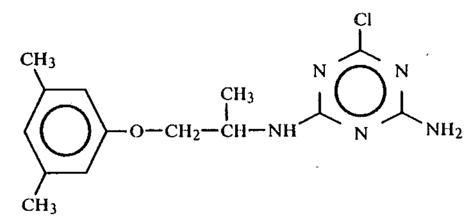 | $C_{14}H_{18}N_5OCl$ | 307.8 |

TABLE 2-continued

Triazine Derivatives

| Preparation Example No. | Compound produced | Name | Amount (g) | Yield (%) | Melting Point(°C.) | Elemental Analysis*(%) C | H | N | Structure | Molecular Formula | Molecular Weight |
|---|---|---|---|---|---|---|---|---|---|---|---|
| 11 | Compound 11 | 2-Amino-4-chloro-6-[2-(3'-t-butyl-phenoxy)-1-methyl-ethylamino]-s-triazine | 3.16 | 94 | 135.7~137.1 | 57.0 (57.2) | 6.4 (6.6) | 20.6 (20.9) | 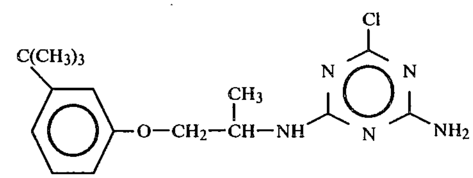 | $C_{16}H_{22}N_5OCl$ | 335.8 |
| 12 | Compound 12 | 2-Amino-4-chloro-6-[2-(3'-phenylphenoxy)-1-methyl-ethylamino]-s-triazine | 3.32 | 93 | — | 60.2 (60.6) | 5.6 (5.4) | (19.9) (19.6) | 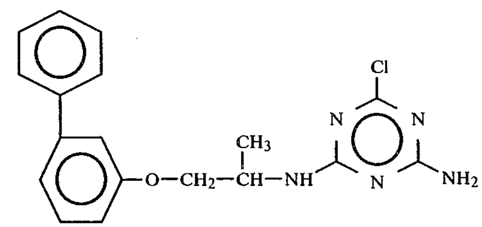 | $C_{18}H_{19}N_5OCl$ | 356.8 |
| 13 | Compound 13 | 2-Amino-4-chloro-6-[2-(3'-phenoxy-phenoxy)-1-methyl-ethylamino]-s-triazine | 3.43 | 92 | 156.5~157.1 | 58.3 (58.0) | 5.0 (5.1) | 18.6 (18.8) | 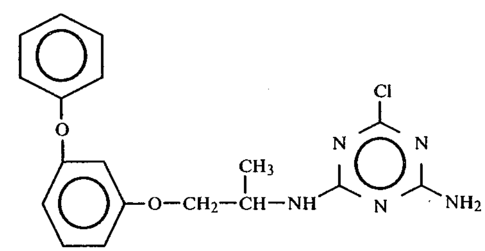 | $C_{18}H_{19}N_5O_2Cl$ | 372.8 |
| 14 | Compound 14 | 2-Amino-4-chloro-6-[2-(3'trifluoro-methylphenoxy)-1-methylethylamino]-s-triazine | | 93 | 166.3~167.1 | 45.1 (44.9) | 4.0 (3.8) | 19.7 (20.1) | 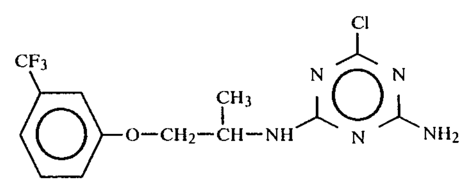 | $C_{13}H_{13}N_5OClF_3$ | 347.7 |

TABLE 2-continued
Triazine Derivatives

| Preparation Example No. | Compound produced | Name | Amount (g) | Yield (%) | Melting Point (°C.) | Elemental Analysis*(%) C | H | N | Structure | Molecular Formula | Molecular Weight |
|---|---|---|---|---|---|---|---|---|---|---|---|
| 15 | Compound 15 | 2-Amino-4-chloro-6-[2-(2'-methyl-phenylthio)-1-methyl-ethylamino]-s-triazine | 2.91 | 94 | 136.7~138.4 | 50.6 (50.4) | 5.0 (5.2) | 22.9 (22.6) | 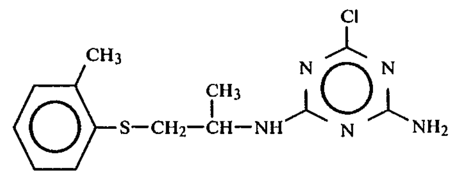 | $C_{13}H_{16}N_5SCl$ | 309.8 |
| 16 | Compound 16 | 2-Amino-4-methylthio-6-[2-(3'-methyl-phenoxy)-1-methyl-ethylamino]-s-triazine | 2.81 | 92 | colorless resinoid | 55.5 (55.1) | 6.1 (6.3) | 22.8 (22.9) | 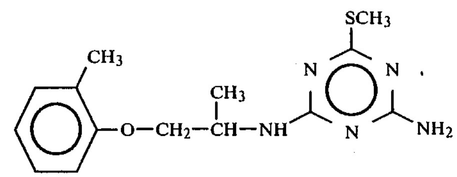 | $C_{14}H_{19}N_5OS$ | 305.4 |
| 17 | Compound 17 | 2-Amino-4-methylthio-6-[2-(2'-methyl-phenoxy)-1-methyl-ethylamino]-s-triazine | 2.84 | 93 | colorless resinoid | 55.4 (55.1) | 6.2 (6.3) | 22.7 (22.9) | 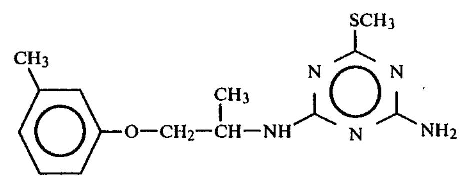 | $C_{14}H_{19}N_5OS$ | 305.4 |
| 18 | Compound 18 | 2-Amino-4-methylthio-6-[2-(4'-methyl-phenxoy)-1-methyl-ethylamino]-s-triazine | 2.84 | 93 | 175.0~177.9 | 55.0 (55.1) | 6.4 (6.3) | 22.6 (22.9) | 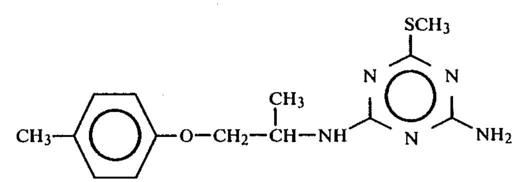 | $C_{14}H_{19}N_5OS$ | 305.4 |
| 19 | Compound 19 | 2-Amino-4-methylthio-6-[2-(2',3'-dimethyl-phenoxy)-1-methyl-ethylamino]-s-triazine | 3.00 | 94 | colorless resinoid | 56.1 (56.4) | 6.8 (6.6) | 22.1 (21.9) | 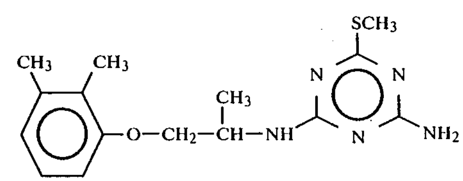 | $C_{15}H_{21}N_5OS$ | 319.4 |

TABLE 2-continued

Triazine Derivatives

| Preparation Example No. | Compound produced | Name | Amount (g) | Yield (%) | Melting Point (°C.) | Elemental Analysis*(%) C | H | N | Structure | Molecular Formula | Molecular Weight |
|---|---|---|---|---|---|---|---|---|---|---|---|
| 20 | Compound 20 | 2-Amino-4-methylthio-6-(2-phenoxy-1-methyl-ethylamino]-s-triazine | 2.65 | 92 | colorless resinoid | 54.0 (54.2) | 4.7 (4.9) | 24.6 (24.3) | 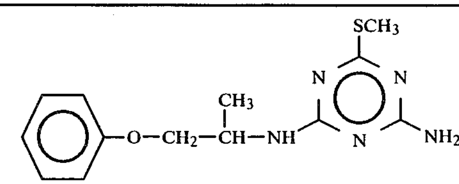 | $C_{13}H_{17}N_5OS$ | 288.3 |
| 21 | Compound 21 | 2-Amino-4-methylthio-6-[2-(3',4'-dimethyl-phenoxy)-1-methyl-ethylamino]-s-triazine | 3.00 | 94 | colorless resinoid | 56.8 (56.4) | 6.3 (6.6) | 21.6 (21.9) | 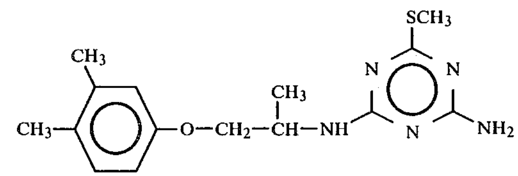 | $C_{15}H_{21}N_5OS$ | 319.4 |
| 22 | Compound 22 | 2-Amino-4-methylthio-6-[2-(3'-methoxy-phenoxy)-1-methyl-ethylamino]-s-triazine | 2.96 | 92 | colorless resinoid | 52.0 (52.3) | 6.2 (6.0) | 21.6 (21.8) | 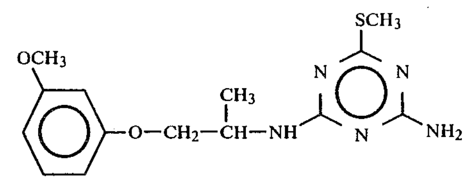 | $C_{14}H_{19}N_5O_2S$ | 321.4 |
| 23 | Compound 23 | 2-Amino-4-methylthio-6-[2-(3'-chloro-phenoxy)-1-methyl-ethylamino]-s-triazine | 3.03 | 93 | colorless resinoid | 48.2 (47.9) | 5.1 (5.0) | 21.1 (21.5) | 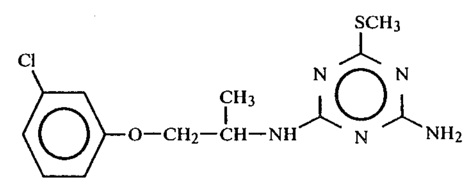 | $C_{13}H_{16}N_5OSCl$ | 325.8 |
| 24 | Compound 24 | 2-Amino-4-methylthio-6-[2-(2',5'-dimethyl-phenoxy)-1-methyl-ethylamino]-s-triazine | 3.00 | 94 | colorless resinoid | 56.7 (56.4) | 6.7 (6.6) | 21.7 (21.9) | 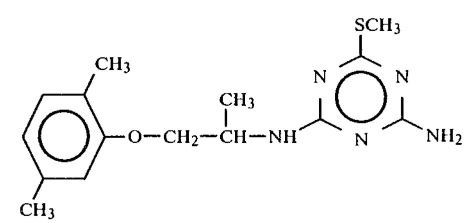 | $C_{15}H_{21}N_5OS$ | 319.4 |

TABLE 2-continued

Triazine Derivatives

| Preparation Example No. | Compound produced | Name | Amount (g) | Yield (%) | Melting Point (°C.) | Elemental Analysis*(%) C | H | N | Structure | Molecular Formula | Molecular Weight |
|---|---|---|---|---|---|---|---|---|---|---|---|
| 25 | Compound 25 | 2-Amino-4-methylthio-6-[2-(3',5'-dimethyl-phenoxy)-1-methyl-ethylamino]-s-triazine | 2.97 | 93 | 122.1~124.1° C. | 56.2 (56.4) | 6.8 (6.6) | 21.6 (21.9) | 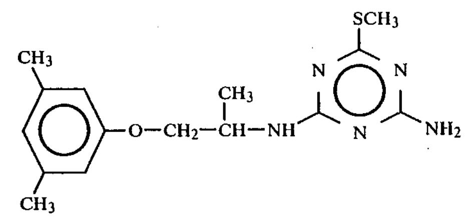 | $C_{15}H_{21}N_5OS$ | 319.4 |
| 26 | Compound 26 | 2-Amino-4-methylthio-6-[2-(3'-t-butyl-phenoxy)-1-methyl-ethylamino]-s-triazine | 3.27 | 94 | colorless resinoid | 59.0 (58.8) | 7.1 (7.3) | 20.5 (20.2) | 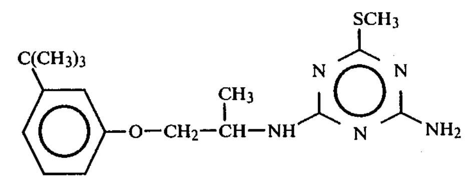 | $C_{17}H_{25}N_5OS$ | 347.5 |
| 27 | Compound 27 | 2-Amino-4-methylthio-6-[2-(3'-phenyl-phenoxy)-1-methyl-ethylamino]-s-triazine | 3.39 | 92 | colorless resinoid | 61.6 (61.9) | 6.2 (6.0) | 19.2 (19.0) | 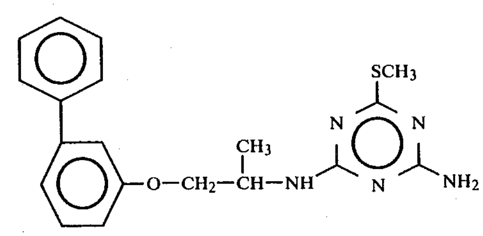 | $C_{19}H_{22}N_5OS$ | 368.5 |
| 28 | Compound 28 | 2-Amino-4-methylthio-6-[2-(3'-phenoxy-phenoxy)-1-methyl-ethylamino]-s-triazine | 3.58 | 93 | colorless resinoid | 59.8 (59.4) | 5.6 (5.8) | 19.0 (18.2) | 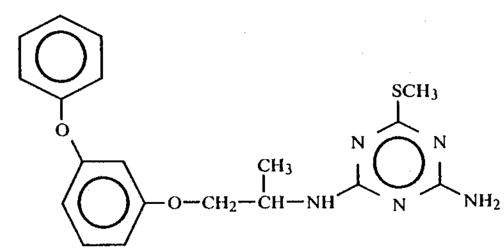 | $C_{19}H_{22}N_5O_2S$ | 384.5 |

TABLE 2-continued

Triazine Derivatives

| Preparation Example No. | Compound produced | Name | Amount (g) | Yield (%) | Melting Point(°C.) | Elemental Analysis*(%) C | H | N | Structure | Molecular Formula | Molecular Weight |
|---|---|---|---|---|---|---|---|---|---|---|---|
| 29 | Compound 29 | 2-Amino-4-methylthio-6-[2-(3'-trifluoromethylphenoxy)-1-methyl-ethylamino]-s-triazine | 3.38 | 94 | colorless resinoid | 46.5 (46.8) | 4.7 (4.5) | 19.7 (19.5) | 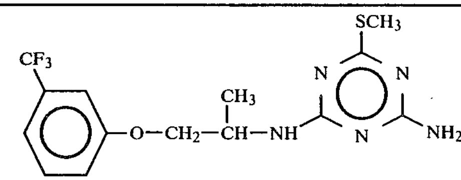 | $C_{14}H_{16}N_5OSF_3$ | 359.4 |
| 30 | Compound 30 | 2-Amino-4-methylthio-6-[2-(2'-methylphenylthio)-1-methyl-ethylamino]-s-triazine | 2.99 | 93 | colorless resinoid | 52.5 (52.3) | 5.8 (6.0) | 22.1 (21.8) | 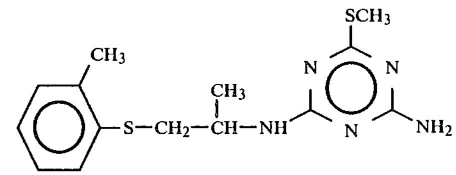 | $C_{14}H_{19}N_5S_2$ | 321.5 |
| 31 | Compound 31 | 2-Amino-4-methoxy-6-[2-(3'-methylphenoxy)isopropyl-amino]-s-triazine | 2.72 | 94 | 222.0~223.5 | 57.7 (58.1) | 6.8 (6.6) | 24.5 (24.2) | 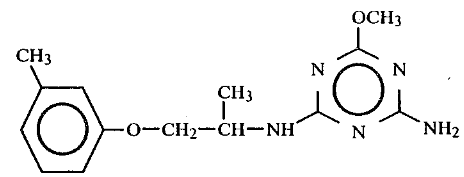 | $C_{14}H_{19}N_5O_2$ | 289.3 |

*The numerical value in the brackets means calculated value.

TABLE 3

| Preparation Example No. | Compound produced | Infrared Absorption Spectrum*1 (cm$^{-1}$) s-triazine | Proton Nuclear Magnetic Resonance Spectrum*2 (ppm) |
|---|---|---|---|
| 16 | 16 | 1540 | 1.33 (3H, d, CHC$\underline{H}_3$), 2.28 (3H, s, φ-C$\underline{H}_3$), 2.38 (3H, s, SC$\underline{H}_3$), 3.63~4.78 (3H, m, OC$\underline{H}_2$C$\underline{H}$), 5.80~7.36 (7H, m, C$_6\underline{H}_4$, N$\underline{H}$, N$\underline{H}_2$) |
| 17 | 17 | 1550 | 1.35 (3H, d, CHC$\underline{H}_3$), 2.16 (3H, s, φ-C$\underline{H}_3$), 2.36 (3H, s, SC$\underline{H}_3$), 3.78~4.78 (3H, m, OC$\underline{H}_2$C$\underline{H}$), 6.50~7.33 (4H, m, C$_6\underline{H}_4$) |
| 18 | 18 | 1540 | 1.30 (3H, d, CHC$\underline{H}_3$), 2.23 (3H, s, φ-C$\underline{H}_3$), 2.35 (3H, s, SC$\underline{H}_3$), 3.65~4.87 (3H, m, OC$\underline{H}_2$C$\underline{H}$), 6.55~7.25 (4H, m, C$_6\underline{H}_4$) |
| 19 | 19 | 1540 | 1.34 (3H, d, CHC$\underline{H}_3$), 2.17 (3H, s, φ-C$\underline{H}_3$), 2.26 (3H, s, φ-C$\underline{H}_3$), 2.41 (3H, s, SC$\underline{H}_3$), 3.66~4.84 (3H, m, OC$\underline{H}_2$C$\underline{H}$), 6.40~7.00 (3H, m, C$_6\underline{H}_3$) |
| 20 | 20 | 1540 | 1.34 (3H, d, CHC$\underline{H}_3$), 2.39 (3H, s, SC$\underline{H}_3$), 3.64~4.86 (3H, m, OC$\underline{H}_2$C$\underline{H}$), 5.73~7.50 (8H, m, C$_6\underline{H}_5$, N$\underline{H}$, N$\underline{H}_2$) |
| 21 | 21 | 1540 | 1.31 (3H, d, CHC$\underline{H}_3$), 2.14 (6H, s, φ-C$\underline{H}_3$ × 2), 2.37 (3H, s, SC$\underline{H}_3$), 3.45~4.74 (3H, m, OC$\underline{H}_2$C$\underline{H}$), 5.93~7.15 (6H, m, C$_6\underline{H}_3$, N$\underline{H}$, N$\underline{H}_2$) |
| 22 | 22 | 1550 | 1.31 (3H, d, CHC$\underline{H}_3$), 1.34 (3H, s, SC$\underline{H}_3$), 3.54~4.64 (3H, m, OC$\underline{H}_2$C$\underline{H}$), 4.73 (H, s, OC$\underline{H}_3$), 5.74~7.42 (7H, m, C$_6\underline{H}_4$, N$\underline{H}$, N$\underline{H}_2$) |
| 23 | 23 | 1540 | 1.30 (3H, d, CHC$\underline{H}_3$), 2.33 (3H, s, SC$\underline{H}_3$) 3.70~4.75 (3H, m, OC$\underline{H}_2$C$\underline{H}$), 6.50~7.40 (4H, m, C$_6\underline{H}_4$) |
| 24 | 24 | 1540 | 1.33 (3H, d, CHC$\underline{H}_3$), 2.10 (3H, s, φ-C$\underline{H}_3$), 2.23 (3H, s, φ-C$\underline{H}_3$), 2.33 (3H, s, SC$\underline{H}_3$), 3.64~4.47 (3H, m, OC$\underline{H}_2$C$\underline{H}$), 6.40~7.03 (3H, m, C$_6\underline{H}_3$) |
| 25 | 25 | 1540 | 1.38 (3H, d, CHC$\underline{H}_3$), 2.21 (6H, s, φ-C$\underline{H}_3$ × 2), 2.37 (3H, s, SC$\underline{H}_3$), 3.63~4.75 (3H, m, OC$\underline{H}_2$C$\underline{H}$), 5.84~6.75 (6H, m, C$_6\underline{H}_3$, N$\underline{H}$, N$\underline{H}_2$) |
| 26 | 26 | 1540 | 1.29 [9H, s, C(C$\underline{H}_3$)$_3$], 1.34 (3H, d, CHC$\underline{H}_3$), 2.40 (3H, s, SC$\underline{H}_3$), 3.82~4.61 (3H, m, OC$\underline{H}_2$C$\underline{H}$), 6.54~7.36 (4H, m, C$_6\underline{H}_4$) |
| 27 | 27 | 1530 | 1.26 (3H, d, CHC$\underline{H}_3$), 2.32 (3H, s, SC$\underline{H}_3$), 3.97 (2H, m, OC$\underline{H}_2$), 4.37 (1H, m, =C$\underline{H}$—), 6.50~7.70 (9H, m, C$_6\underline{H}_4$, C$_6\underline{H}_5$) |
| 28 | 28 | 1530 | 1.30 (3H, d, —CHC$\underline{H}_3$), 2.35 (3H, s, SC$\underline{H}_3$), 3.50~4.70 (3H, m, OC$\underline{H}_2$C$\underline{H}$), 6.25~7.55 (9H, m, C$_6\underline{H}_4$, C$_6\underline{H}_5$) |
| 29 | 29 | 1575 | 1.35 (3H, d, CHC$\underline{H}_3$), 2.40 (3H, s, SC$\underline{H}_3$), 4.05 (2H, m, OC$\underline{H}_2$CH), 4.50 (1H, m, OCH$_2$C$\underline{H}$), 6.90~7.70 (4H, m, C$_6\underline{H}_4$) |
| 30 | 30 | 1550 | 1.33 (3H, d, CHC$\underline{H}_3$), 2.31 (6H, φ-C$\underline{H}_3$, SC$\underline{H}_3$), 2.65~3.40 (2H, m, SC$\underline{H}_2$), 3.95~4.19 (1H, m, SCH$_2$C$\underline{H}$), 5.90~7.60 (7H, m, C$_6\underline{H}_4$, N$\underline{H}$, N$\underline{H}_2$) |

*1Potassium bromide tablet method
*2Solvent: chloroform-D$_1$, acteone-D$_6$
Internal standard: tetramethylsilane(TMS)

EXAMPLES 1 TO 23

(1) Preparation of herbicide:

97 parts by weight of talc (trade name: Zeaklite) as carrier, 1.5 parts by weight of alkylarylsulfonate as surfactant (trade name: Neo pelex, manufactured by Kao-Atlas KK) and 1.5 parts by weight of a mixture of nonion type and anion type surfactant (trade name: Sorpol 800A, manufactured by Toho Kagaku Kogyo KK) were homogeneously ground and mixed to obtain a carrier for a wettable powder.

A herbicidal wettable powder was prepared by grinding and mixing homogeneously 90 parts by weight of the above obtained carrier for the wettable powder with 10 parts by weight of one of the triazine derivatives prepared as reported in the Preparation Examples 1 to 31.

(2) Results of biological tests:

Treatment under submerged condition

A 1/15500-are porcelain pot was filled with the soil of a paddy field and seeds of *Echinochloa crus-galli L., Cyperus difformis L., Rotala indica* (Willd.) *Koehne* var. *uligirosa* (Miq.) *Koehne., Scirpus juncoides Roxb.* var. *Hotarui Ohwi* and *Monochoria vaginalis Presl* var. *plantaginea (Roxb.) Solms-Laub.* were sown uniformly in the upper layer of the soil. And then the tubers of *Cyperus serotinus Rottb.* and *Sagittaria pygmaea Miq.* were planted in the soil, thereafter young rice plants of the second-leaf stage were transplanted.

When the weeds were germinated, a predetermined amount of a diluted solution of a herbicide prepared as reported in paragraph (1) hereinbefore was uniformly applied dropwise to the surface of the water and then the pot was kept in a green-house and sprinkled with water at appropriate time intervals.

Table 4 reports the evaluation of the herbicidal effect and the phytotoxicity to the paddy rice plants at 20 days after application of the herbicide. In Table 4, the amount of the herbicide is 50 grams/10 ares to 400 grams/10 ares as the amount of the active component. The phytotoxicity and herbicidal effect were evaluated respectively according to the following scale by determining the dry weight.

| Phytotoxicity to the paddy rice plants: | | |
|---|---|---|
| 0 | ratio to an untreated pot | 100% |
| 1 | ratio to an untreated pot | 95–99% |
| 2 | ratio to an untreated pot | 90–94% |
| 3 | ratio to an untreated pot | 80–89% |

| | | -continued | |
|---|---|---|---|
| 4 | ratio to an untreated pot | 60-79% | |
| 5 | ratio to an untreated pot | 50-69% | |
| Herbicidal effect: | | | |
| 0 | ratio to the untreated pot | 100% | |
| 1 | ratio to the untreated pot | 61-99% | |
| 2 | ratio to the untreated pot | 21-60% | |
| 3 | ratio to the untreated pot | 11-20% | |

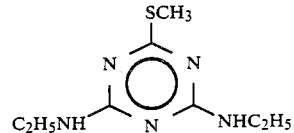

(A)

TABLE 4

| No. | Compound as effective component | Amount of herbicide (gram/10 ares) | Herbicidal effect | | | | | | Phytotoxicity to the paddy rice plants |
|---|---|---|---|---|---|---|---|---|---|
| | | | *Echinochloa crus-galli* L. | *Cyperus serotinus* Rottb. | *Scirpus juncoides* Roxb. var Hotarui Ohwi | *Cyperus difformis* L. | Annual broadleaf weeds | *Sagittaria pygmaea* Miq. | |
| Example 1 | Compound 1 | 400 | 5 | 5 | 5 | 5 | 5 | 5 | 0 |
| | | 200 | 5 | 5 | 5 | 5 | 5 | 4 | 0 |
| Example 2 | Compound 4 | 400 | 5 | 5 | 5 | 5 | 5 | 5 | 0 |
| | | 200 | 5 | 5 | 5 | 5 | 5 | 5 | 0 |
| Example 3 | Compound 7 | 400 | 5 | 5 | 5 | 5 | 5 | 5 | 0 |
| | | 200 | 5 | 5 | 5 | 5 | 5 | 5 | 0 |
| Example 4 | Compound 9 | 400 | 5 | 5 | 5 | 5 | 5 | 5 | 0 |
| | | 200 | 5 | 5 | 5 | 5 | 5 | 5 | 0 |
| Example 5 | Compound 10 | 400 | 5 | 5 | 5 | 5 | 5 | 5 | 0 |
| | | 200 | 5 | 5 | 5 | 5 | 5 | 5 | 0 |
| Example 6 | Compound 11 | 400 | 5 | 3 | 5 | 5 | 5 | 4 | 0 |
| | | 200 | 5 | 3 | 5 | 5 | 5 | 4 | 0 |
| Example 7 | Compound 12 | 400 | 5 | 5 | 4 | 5 | 5 | 4 | 0 |
| | | 200 | 5 | 5 | 4 | 5 | 5 | 3 | 0 |
| Example 8 | Compound 14 | 400 | 5 | 5 | 5 | 5 | 5 | 5 | 0 |
| | | 200 | 5 | 5 | 5 | 5 | 5 | 4 | 0 |
| Example 9 | Compound 16 | 100 | 5 | 5 | 5 | 5 | 5 | 5 | 0 |
| | | 50 | 5 | 5 | 5 | 5 | 5 | 5 | 0 |
| Example 10 | Compound 17 | 100 | 5 | 5 | 5 | 5 | 5 | 5 | 0 |
| | | 50 | 5 | 5 | 5 | 5 | 5 | 4 | 0 |
| Example 11 | Compound 19 | 100 | 5 | 5 | 5 | 5 | 5 | 5 | 0 |
| | | 50 | 5 | 5 | 5 | 5 | 5 | 5 | 0 |
| Example 12 | Compound 20 | 400 | 5 | 5 | 5 | 5 | 5 | 5 | 0 |
| | | 200 | 5 | 5 | 5 | 5 | 5 | 5 | 0 |
| Example 13 | Compound 21 | 100 | 5 | 5 | 5 | 5 | 5 | 5 | 0 |
| | | 50 | 5 | 5 | 5 | 5 | 5 | 5 | 0 |
| Example 14 | Compound 22 | 100 | 5 | 5 | 5 | 5 | 5 | 5 | 0 |
| | | 50 | 5 | 4 | 4 | 5 | 5 | 4 | 0 |
| Example 15 | Compound 23 | 400 | 5 | 5 | 3 | 5 | 5 | 3 | 0 |
| | | 200 | 5 | 5 | 3 | 5 | 5 | 3 | 0 |
| Example 16 | Compound 24 | 100 | 5 | 5 | 5 | 5 | 5 | 5 | 0 |
| | | 50 | 5 | 5 | 5 | 5 | 5 | 5 | 0 |
| Example 17 | Compound 25 | 100 | 5 | 5 | 5 | 5 | 5 | 5 | 0 |
| | | 50 | 5 | 5 | 5 | 5 | 5 | 5 | 0 |
| Example 18 | Compound 26 | 400 | 5 | 5 | 5 | 5 | 5 | 5 | 0 |
| | | 200 | 5 | 5 | 5 | 5 | 5 | 5 | 0 |
| Example 19 | Compound 27 | 400 | 5 | 5 | 5 | 5 | 5 | 4 | 0 |
| | | 200 | 5 | 5 | 5 | 5 | 5 | 4 | 0 |
| Example 20 | Compound 28 | 400 | 5 | 5 | 4 | 5 | 5 | 5 | 0 |
| | | 200 | 5 | 5 | 4 | 5 | 5 | 5 | 0 |
| Example 21 | Compound 29 | 400 | 5 | 5 | 5 | 5 | 5 | 4 | 0 |
| | | 200 | 5 | 5 | 5 | 5 | 5 | 4 | 0 |
| Example 22 | Compound 30 | 400 | 5 | 5 | 5 | 5 | 5 | 5 | 0 |
| | | 200 | 5 | 5 | 5 | 5 | 5 | 5 | 0 |
| Example 23 | Compound 31 | 400 | 5 | 5 | 5 | 5 | 5 | 5 | 0 |
| | | 200 | 5 | 5 | 5 | 5 | 5 | 4 | 0 |
| Comparative Example 1 | Simetryn | 400 | 5 | 2 | 3 | 5 | 5 | 3 | 5 |
| | | 200 | 5 | 2 | 3 | 5 | 5 | 3 | 5 |
| | | 100 | 5 | 2 | 3 | 5 | 5 | 3 | 2 |
| | | 50 | 1 | 0 | 0 | 5 | 5 | 0 | 0 |

| 4 | ratio to the untreated pot | 1-10% |
| 5 | ratio to the untreated pot | 0% |

COMPARATIVE EXAMPLE 1

The same procedure as in Example 1 was carried out except that 2-methylthio-4,6-bis(ethylamino)-s-triazine (common name: Simetryn) shown in the following formula (A) was used in place of the triazine derivative prepared as reported in the Preparation Example 1. The results are shown in Table 4.

What is claimed is:

1. A triazine derivative represented by the formula (I):

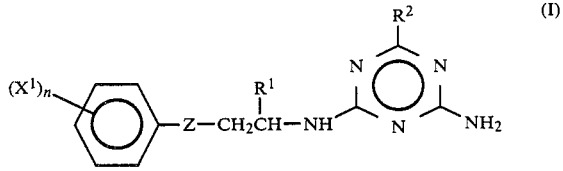

(wherein $X^1$ is a hydrogen atom, an alkyl group having 1 to 4 carbon atoms, an alkoxy group having 1 to 4 carbon atoms, a halogen atom, a haloalkyl group having 1 to 4 carbon atoms, a phenyl group, or a phenoxy group; n is an integer of 1 to 5 and when n is 2 or more, $X^1$s may be same or different; Z is an oxygen atom or a sulfur atom; $R^1$ is an alkyl group having 1 to 4 carbon atoms; and $R^2$ is a halogen atom, an alkoxy group having 1 to 4 carbon atoms, or an alkylthio group having 1 to 4 carbon atoms).

2. The triazine derivative of claim 1 wherein $X^1$ is selected from a methyl group, an ethyl group, a n-propyl group, an isopropyl group, a n-butyl group, an isobutyl group, a sec-butyl group, a tert-butyl group, a methoxy group, an ethoxy group, a propoxy group, a butoxy group, a trifluoromethyl group, a trichloromethyl group, a monochloromethyl group, a monobromomethyl group, a monofluoromethyl group, and a pentafluoroethyl group.

3. The triazine derivative of claim 1 wherein n is 1 or 2.

4. The triazine derivative of claim 1 wherein $R^1$ is methyl group or an ethyl group.

5. The triazine derivative of claim 1 wherein $R^2$ is selected from a methylthio group, an ethylthio group, a propylthio group, and a butylthio group.

6. The triazine derivative of claim 2 wherein
n is 1 or 2; $R^1$ is methyl or ethyl; and
$R^2$ is methylthio, ethylthio, propylthio or butylthio.

7. The triazine derivative of claim 1 having the formula:

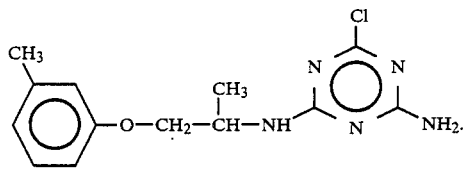

8. The triazine derivative of claim 1 having the formula:

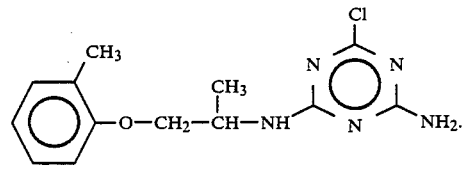

9. The triazine derivative of claim 1 having the formula:

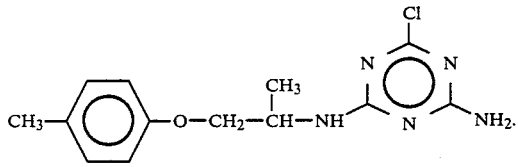

10. The triazine derivative of claim 1 having the formula:

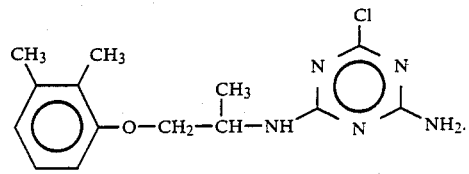

11. The triazine derivative of claim 1 having the formula:

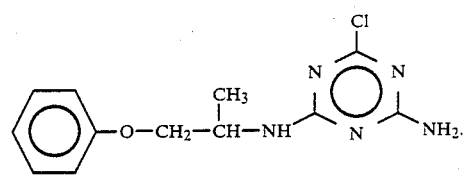

12. The triazine derivative of claim 1 having the formula:

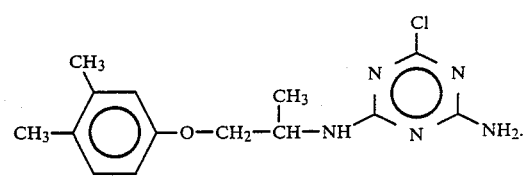

13. The triazine derivative of claim 1 having the formula:

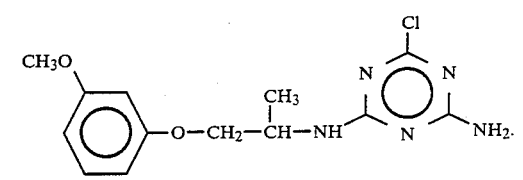

14. The triazine derivative of claim 1 having the formula:

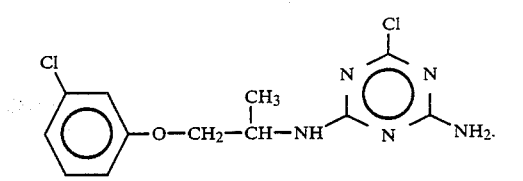

15. The triazine derivative of claim 1 having the formula:

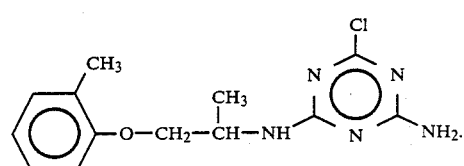

16. The triazine derivative of claim 1 having the formula:

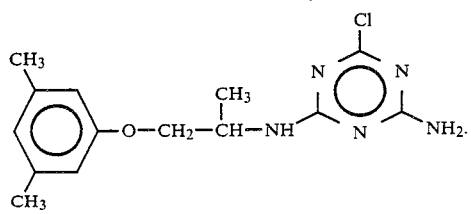

17. The triazine derivative of claim 1 having the formula:

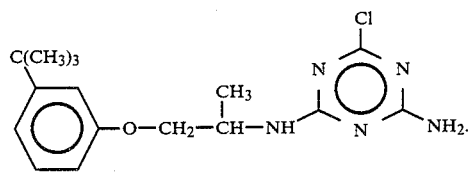

18. The triazine derivative of claim 1 having the formula:

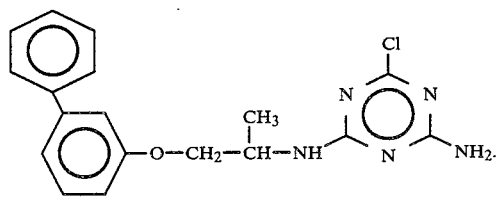

19. The triazine derivative of claim 1 having the formula:

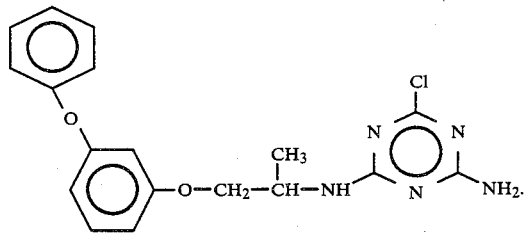

20. The triazine derivative of claim 1 having the formula:

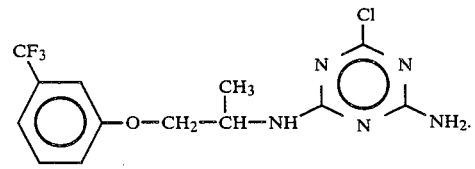

21. The triazine derivative of claim 1 having the formula:

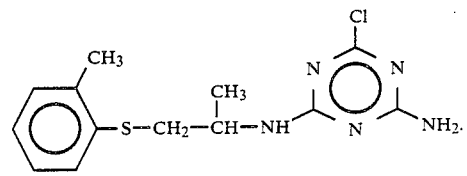

22. The triazine derivative of claim 1 having the formula:

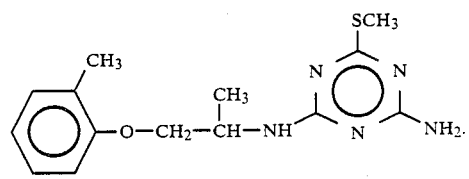

23. The triazine derivative of claim 1 having the formula:

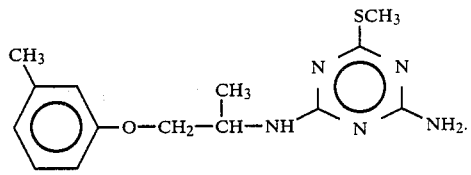

24. The triazine derivative of claim 1 having the formula:

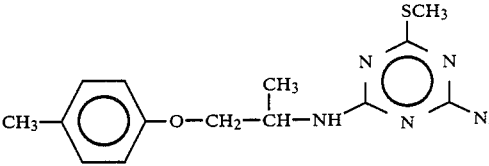

25. The triazine derivative of claim 1 having the formula:

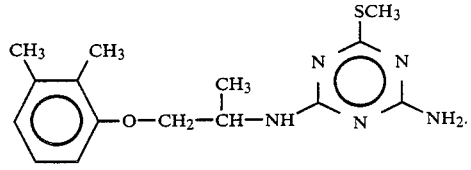

26. The triazine derivative of claim 1 having the formula:

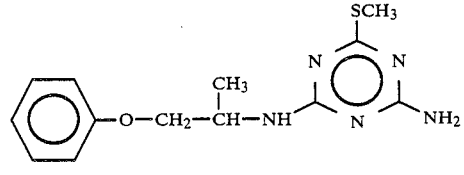

27. The triazine derivative of claim 1 having the formula:

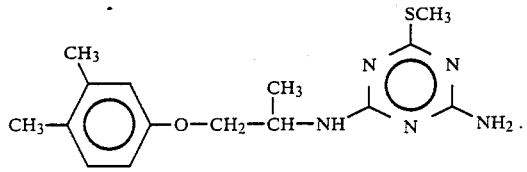

28. The triazine derivative of claim 1 having the formula:

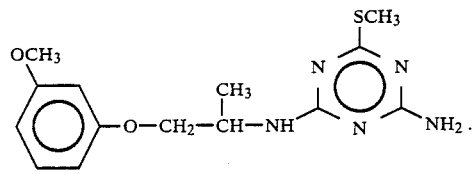

29. The triazine derivative of claim 1 having the formula:

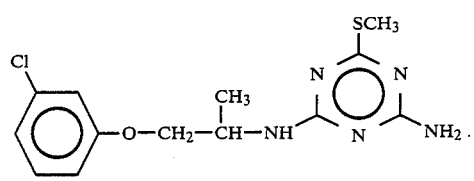

30. The triazine derivative of claim 1 having the formula:

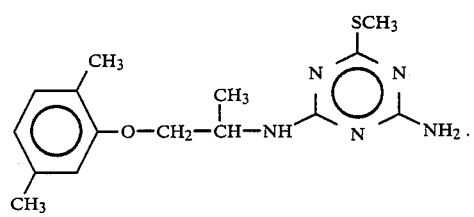

31. The triazine derivative of claim 1 having the formula:

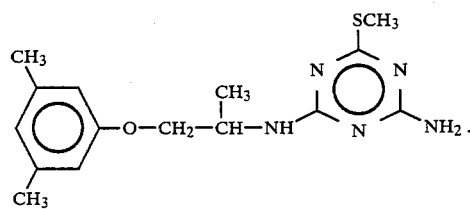

32. The triazine derivative of claim 1 having the formula:

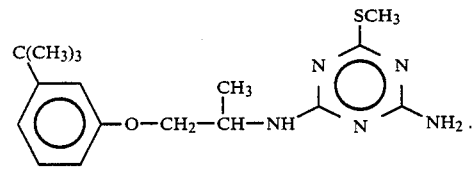

33. The triazine derivative of claim 1 having the formula:

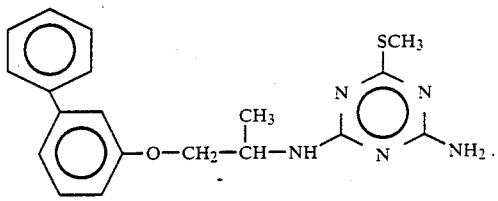

34. The triazine derivative of claim 1 having the formula:

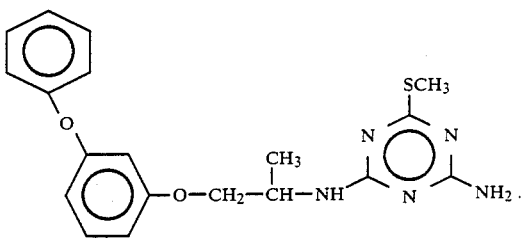

35. The triazine derivative of claim 1 having the formula:

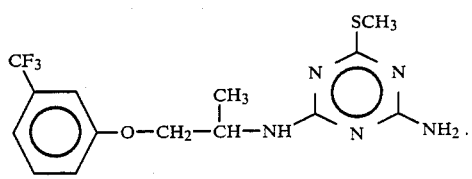

36. The triazine derivative of claim 1 having the formula:

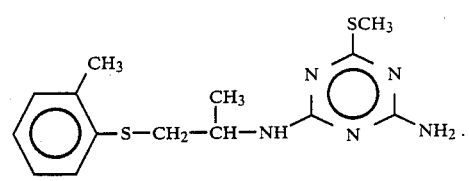

37. The triazine derivative of claim 1 having the formula:

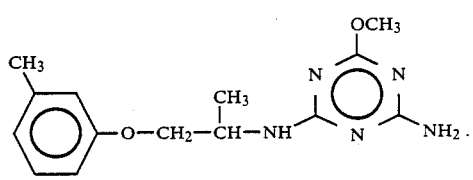

38. A herbicidal composition comprising, as a herbicidally effective component, at least one triazine derivative represented by the formula (I):

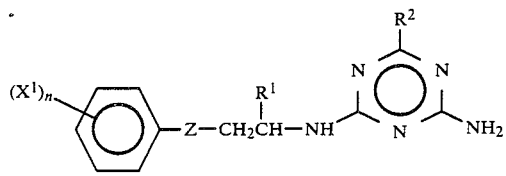
(I)

(wherein $X^1$ is a hydrogen atom, an alkyl group having 1 to 4 carbon atoms, an alkoxy group having 1 to 4 carbon atoms, a halogen atom, a haloalkyl group having 1 to 4 carbon atoms, a phenyl group, or a phenoxy group; n is an integer of 1 to 5 and when n is 2 or more, $X^1$s may be the same or different; Z is an oxygen atom or a sulfur atom; $R^1$ is an alkyl group having 1 to 4 carbon atoms; and $R^2$ is a halogen atom, an alkoxy group having 1 to 4 carbon atoms, or an alkylthio group having 1 to 4 carbon atoms) and a herbicidal carrier.

39. A method of controlling the growth of undesired vegetation in rice paddy soil without harming the rice plants which comprises applying to said rice paddy soil a herbicidally effective amount of a triazine derivative of claim 1.

* * * * *

UNITED STATES PATENT AND TRADEMARK OFFICE
CERTIFICATE OF CORRECTION

PATENT NO. : 4,844,731

DATED : July 4, 1989

INVENTOR(S) : TAKEMATSU et al

It is certified that error appears in the above-identified patent and that said Letters Patent is hereby corrected as shown below:

Title Page: [73] Assignee: Replace "Idemitsu Company Co., Ltd." with --Idemitsu Kosan Co., Ltd.--.

Column 33, line 6: before "same" insert --the--.

Column 33, line 25: before "methyl group" insert --a--.

Signed and Sealed this

Twenty-fourth Day of September, 1991

Attest:

HARRY F. MANBECK, JR.

Attesting Officer

Commissioner of Patents and Trademarks